United States Patent [19]

Goodman et al.

[11] 4,376,719

[45] Mar. 15, 1983

[54] PROCESS FOR THE PRODUCTION OF AQUEOUS DISPERSIONS OF SOLID FREE RADICAL-GENERATING INITIATORS

[75] Inventors: Donald Goodman, Flemington, N.J.; Mario Q. Ceprini, Cedarhurst; Samuel Hoch, Brooklyn, both of N.Y.; Marvin Koral, Warren, N.J.

[73] Assignee: Tenneco Chemicals, Inc., Piscataway, N.J.

[21] Appl. No.: 283,589

[22] Filed: Jul. 15, 1981

[51] Int. Cl.³ .......................... C08F 4/34; C08F 4/04; C08F 14/06; C08F 2/20

[52] U.S. Cl. .................................. 252/426; 526/230; 526/230.5; 526/231; 526/232; 526/232.1; 526/236; 526/344.2

[58] Field of Search ..................... 252/426; 526/344.2

[56] References Cited

U.S. PATENT DOCUMENTS

| | | | |
|---|---|---|---|
| 3,825,509 | 7/1974 | Miller | 526/344.2 |
| 4,092,470 | 5/1978 | Oosterwijk et al. | 526/344.2 |
| 4,143,224 | 3/1979 | Klippert et al. | 526/344.2 |
| 4,232,141 | 11/1980 | Koyanagi et al. | 526/344.2 |

*Primary Examiner*—P. E. Konopka
*Attorney, Agent, or Firm*—Evelyn Berlow

[57] ABSTRACT

Stable aqueous dispersions of free radical-generating polymerization initiators that are solid at temperatures above 0° C. are prepared safely and efficiently by homogenizing a suspension of the initiator in an aqueous system that contains small amounts of a suspending agent and a wetting agent.

5 Claims, No Drawings

PROCESS FOR THE PRODUCTION OF AQUEOUS DISPERSIONS OF SOLID FREE RADICAL-GENERATING INITIATORS

This invention relates to stable aqueous dispersions of free radical-generating initiators for use in the preparation of vinyl halide resins and to a process for their production.

Vinyl halide resins are commonly prepared by suspension polymerization processes in which a vinyl halide or a mixture of a vinyl halide and a comonomer is polymerized in an aqueous medium in the presence of a monomer-soluble free radical-generating initiator and a dispersing or suspending agent. In these processes, the initiators are usually added to the polymerization mixture as solutions in aliphatic or aromatic organic solvents in order to reduce the hazards involved in handling and storing the very reactive initiators and to assist in their uniform dispersion throughout the polymerization mixture.

The addition to the polymerization mixtures of the initiators as solutions in organic solvents is not desirable, however, in that it is likely that in the filtration, stripping, and drying steps of the polymerization process the organic solvents will enter water streams or the atmosphere.

In view of the present safety standards that require that the amounts of organic compounds that enter water systems or the atmosphere be reduced to very low levels, it has become desirable to provide stable aqueous emulsions or dispersions of the free radical-generating initiators that can be stored and handled safely.

When the compounds that are to be used as free radical-generating initiators in the polymerization of vinyl halides or other olefinic monomers are solid at ambient temperature, it is difficult to prepare stable initiator dispersions because these initiators are ordinarily obtained in the form of lumps, coarse particles, or flakes. In U.S. Pat. No. 4,232,141, Koyangi et al. disclosed a process in which dispersions of solid initiators are prepared by grinding the coarse particles in an inert medium at a temperature not above 0° C. until they have a particle size of 50 microns or smaller and then dispersing the particles in water containing a suspending agent. Because the grinding of the highly reactive polymerization initiators may present hazards of heat-induced decomposition, it is not practical to carry out this process on a commercial scale. In addition, dispersions of solid initiators prepared by the procedure disclosed by Koyangi et al. are often viscous liquids or pastes that cannot easily be pumped into the polymerization reactor and uniformly distributed throughout the polymerization mixture.

In accordance with this invention, it has been found that aqueous dispersions of free radical-generating polymerization initiators that are solid at temperatures above 0° C. can be prepared safely and efficiently by forming a suspension of the initiator in an aqueous system that contains a suspending agent and a wetting agent and homogenizing the resulting suspension. Dispersions prepared in this way are shelf-stable mobile liquids that can be easily pumped into the polymerization reactor and readily dispersed throughout the aqueous polymerization medium. Because the initiator is present in a diluted form during the homogenization step and the heat generated is dissipated through the aqueous medium, the possibility of excessive heat buildup is minimized. In addition, since the dispersions are free from initiator particles that are coarser than about 20 microns, the polymerization of the vinyl halide takes place smoothly and leads to the production of vinyl halide resins having relatively uniform particle size and particle size distribution.

In the practice of this invention, an aqueous dispersion that contains from 10% to 40% and preferably 20% to 30% by weight of a free radical-generating polymerization initiator that is solid at temperatures above 0° C. is formed by adding the initiator to an aqueous system that contains a water-soluble suspending agent and a wetting agent and that is at a temperature in the range of about 5° C. to 30° C. and homogenizing the resulting suspension. The dispersion prepared in this way, which contains very finely divided particles of the initiator, has prolonged shelf-stability when stored at a temperature in the range of about 4°–10° C.

The polymerization initiators that may be dispersed in aqueous systems by the process of this invention include azo compounds, peroxides, peroxydicarbonates, peroxyesters, and the like that are solid at temperatures above 0° C. Illustrative of these initiators are 2,2'-azobis(isobutyronitrile), 2,2'-azobis(2,4-dimethylvaleronitrile), 2,2'-azobis(2,4,4-trimethylvaleronitrile), 2,2'-azobis(4-methoxy-2,4-dimethylvaleronitrile), lauroyl peroxide, decanoyl peroxide, dicumyl peroxide, benzoyl peroxide, 2,4-dichlorobenzoyl peroxide, dicyclohexyl peroxydicarbonate, 2,5-bis(benzoyl peroxy)-hexane, bis-tert.butylcyclohexyl peroxydicarbonate, and the like. A single initiator or a mixture of two or more of these initiators may be present in the aqueous dispersions.

The suspending agents that are used in the practice of the process of this invention are preferably those that are commonly used in the suspension polymerization of vinyl halides in an aqueous medium. These include water-soluble cellulose derivatives, such as methylcellulose, hydroxymethylcellulose, hydroxyethylcellulose, and hydroxypropylcellulose; gelatin; polyvinyl alcohol; starch; methyl vinyl ether-maleic anhydride copolymers; vinyl acetate-maleic anhydride copolymers; metal salts of carboxymethylcellulose and polyacrylic acids; and mixtures thereof. Polyalkylene glycols, such as polyethylene glycols and polypropylene glycols, have also been found to be effective in maintaining stable dispersions of solid initiators. The useful wetting agents include nonionic surfactants, anionic surfactants, and mixtures of nonionic and anionic surfactants. Illustrative of the nonionic surfactants that can be used are polyoxyethylene alkyl ethers, polyoxyethylene alkyl esters, polyoxyethylene alkyl aryl ethers, sorbitan alkyl esters, polyoxyethylene-propylene glycol ethers, polyoxyethylenesorbitan alkyl esters, fatty acid monoglycerides, and mixtures thereof. The anionic surfactants are exemplified by fatty acid soaps, such as sodium oleate and ammonium laurate; sulfates, such as sodium lauryl sulfate and ammonium lauryl sulfate; alkyl aryl sulfonates, such as dodecylbenzene sodium sulfonate and dodecylnaphthalene sodium sulfonate; dialkylsulfosuccinates, such as dioctylsulfosuccinate; alkyl sulfonates; and mixtures thereof. The preferred wetting agents are nonionic surfactants derived from ethylene oxide adducts of alkylphenols, for example, the Triton series of surfactants and the Igepal CO series of surfactants.

The aqueous dispersions may contain from 1% to 5% by weight of a suspending agent and from 0.1% to 2% by weight of a nonionic wetting agent and/or an anionic wetting agent; they may also contain from 8% to 20% by weight of a polyalkylene glycol. The dispersions preferably contain from 1.5% to 2.5% by weight of a suspending agent and from 0.1% to 0.7% by weight of a wetting agent.

Homogenization of the initiator suspension may be effected by applying a shear force to it. Any apparatus that is capable of providing such force may be used for this purpose. Examples of suitable apparatus include homogenizers, colloid mills, high speed pumps, vibratory stirrers, high frequency and ultrasonic oscillators, and the like. Especially satisfactory results have been obtained when a homogenizer was used to apply shearing force to the initiator-containing suspensions. Dispersions prepared in this way generally contain initiator particles that have an average particle size of not more than 10 microns, preferably in the range of 0.1 micron to 2 microns.

The aqueous dispersions of solid polymerization initiators prepared by the process of this invention are as effective as the solid initiators per se and as solutions of these initiators in organic solvents in the polymerization of vinyl halides and other olefinic monomers in aqueous systems by convention polymerization techniques. Their use makes possible safer storage and handling of the active and hazardous initiators as well as more quantitative and safer introduction of the initiators into polymerization reactors.

The invention is further illustrated by the following examples. In these examples, all parts are parts by weight and all percentages are percentages by weight.

EXAMPLE 1

A mixture of 386.5 parts of water and 1 part of nonyl phenoxypoly(ethyleneoxy)ethanol (GAF's Igepal CO-610) was agitated vigorously at 21°–24° C. while 12.5 parts of methylcellulose (Dow's Methocel) was added to it over a 2 to 2.5 hour period. When the solution had been agitated for an additional 30 minutes, 100 parts of 2,2'-azobis(2,4-dimethylvaleronitrile) (duPont's Vazo 52) was added to it over a period of 15 minutes. The resulting suspension was agitated for an additional 15 minutes at 20°–25° C. and then passed through a homogenizer three times, with the size of the homogenizer orifice decreased after each pass. There was obtained 500 parts of a very fine dispersion that contained 20% of the initiator, 2.5% of the suspending agent, and 0.2% of the wetting agent. This product, which had a Gardner-Holdt viscosity at 25° C. of M-N, remained a uniform liquid dispersion after it had been stored at 4°–10° C. for more than 4 weeks.

EXAMPLE 2

A mixture of 77.4 parts of water and 0.1 part of an alkaryl polyether alcohol (Rohm & Haas's Triton X-155) was agitated vigorously at 20°–25° C. while 2.5 parts of methylcellulose was added to it over a 2 to 2.5 hour period. When the solution had been agitated for an additional 30 minutes, 20 parts of 2,2'-azobis(2,4-dimethylvaleronitrile) was added to it over a period of 15 minutes. The suspension was agitated for an additional 15 minutes at 20° C. and then passed through a homogenizer three times, with the size of the homogenizer orifice decreased after each pass. The very fine dispersion that was obtained was a mobile liquid that was stable for more than a week when stored at 4°–10° C.

EXAMPLE 3

The procedure described in Example 2 was repeated except that 0.2 part of the alkaryl polyether alcohol (Triton X-155) was used. The fine dispersion that was obtained was a mobile liquid that was stable for more than 3 days when stored at 4°–10° C.

EXAMPLE 4

A mixture of 77.5 parts of water and 0.5 part of nonylphenoxypoly(ethyleneoxy)ethanol (Igepal CO-610) was agitated vigorously at 21°–24° C. while 2 parts of polyvinyl alcohol (partially hydrolyzed polyvinyl acetate) was added to it over a period of 2 hours. When the solution had been agitated for an additional 30 minutes, 20 parts of 2,2'-azobis(2,4-dimethylvaleronitrile) was added to it over a period of 15 minutes. The suspension was agitated for an additional 15 minutes at 20°–25° C. and then passed through a homogenizer three times, with the size of the homogenizer orifice decreased after each pass. The very fine dispersion that was obtained was a mobile liquid that was stable for more than a week when stored at 4°–10° C.

EXAMPLE 5

A mixture of 77.5 parts of water and 0.5 part of sodium N-methyl-N-oleoyltaurate (GAF's Igepon T-77) was agitated vigorously at 21°–24° C. while 2 parts of methylcellulose (Methocel) was added to it over a 2 hour period. When the solution had been agitated for an additional 30 minutes, 20 parts of 2,2'-azobis(2,4-dimethylvaleronitrile) was added to it over a period of 15 minutes. The suspension was agitated for an additional 15 minutes at 15°–20° C. and then passed through a homogenizer three times, with the size of the homogenizer orifice decreased after each pass. The fine dispersion that was obtained was a mobile liquid that was stable for more than 4 days when stored at 4°–10° C.

EXAMPLE 6

The procedure described in Example 5 was repeated except that 0.7 part of sodium N-methyl-N-oleoyltaurate and 3 parts of methylcellulose were used. The fine dispersion that was obtained was a mobile liquid that was stable for more than 4 days when stored at 4°–10° C.

EXAMPLE 7

A mixture of 59.6 parts of water, 0.7 part of sodium N-methyl-N-oleoyltaurate (Igepon T-77) and 0.7 part of alkaryl polyether alcohol (Triton X-155) was agitated vigorously at 21°–24° C. while 19 parts of polyethylene glycol (average molecular weight 14,000) was added to it over a 2 hour period. When the solution had been agitated for an additional 30 minutes, 20 parts of 2,2'-azobis(2,4-dimethylvaleronitrile) (Vazo 52) was added to it over a period of 15 minutes. The suspension was agitated for an additional 15 minutes at 20°–25° C. and then passed through a homogenizer three times, with the size of the homogenizer orifice decreased after each pass. The fine dispersion that was obtained was a mobile liquid that was stable for more than a week when stored at 4°–10° C.

EXAMPLE 8

The procedure described in Example 7 was repeated except that 3 parts of methylcellulose was added to the solution before the addition of the solid initiator. There was obtained a fine dispersion that was a mobile liquid that was stable for more than a week when stored at 4°–10° C.

EXAMPLE 9

A mixture of 68.65 parts of water and 0.35 part of sodium N-methyl-N-oleoyltaurate (Igepon T-77) was agitated vigorously at 21°–24° C. while 1.5 parts of methylcellulose and 9.5 parts of polyethylene glycol (average molecular weight 14,000) was added to it over a 2 hour period. When the solution had been agitated for an additional 30 minutes, 20 parts of 2,2'-azobis(2,4-dimethylvaleronitrile) (Vazo 52) was added to it over a period of 15 minutes. The suspension was agitated for an additional 15 minutes at 20° C. and then passed through a homogenizer three times, with the size of the homogenizer orifice decreased after each pass. The fine dispersion that was obtained was a mobile liquid that was stable for more than a week when stored at 4°–10° C.

EXAMPLE 10

The procedure of Example 9 was repeated except that the methylcellulose and polyethylene glycol were added to a solution prepared from 67.6 parts of water, 0.7 part of sodium N-methyl-N-oleoyltaurate, and 0.7 part of alkaryl polyether alcohol (Triton X-155). A mobile liquid that was stable at 4°–10° C. for more than a week was obtained.

EXAMPLE 11

A mixture of 58.8 parts of water, 0.35 part of sodium N-methyl-N-oleoyltaurate (Igepon T-77), and 0.35 part of alkaryl polyether alcohol (Triton X-155) was agitated vigorously at 21°–24° C. while 1.5 parts of methylcellulose and 19 parts of polyethylene glycol (average molecular weight 14,000) was added to it over a 2 hour period. When all of the methylcellulose and polyethylene glycol had dissolved, 20 parts of 2,2'-azobis(2,4-dimethylvaleronitrile) was slowly added to the solution. The resulting suspension was homogenized to yield a fine dispersion that was a mobile liquid that was stable for more than a week when stored at 4°–10° C.

EXAMPLE 12

A series of vinyl halide resins was prepared by a standard suspension polymerization procedure using as the initiator either one of the products of Examples 1–11 or solid 2,2'-azobis(2,4-dimethylvaleronitrile). All of the resins prepared had equivalent color, static and dynamic Brabender heat stability, and other physical properties.

What is claimed is:

1. The process for the production of stable aqueous dispersions of free radical-generating polymerization initiators that are solid at temperatures above 0° C. that comprises the steps of
   (a) forming a suspension that contains from 10% to 40% by weight of a free radical-generating polymerization initiator that is solid at temperatures above 0° C. in an aqueous medium that comprises from 1% to 5% by weight of a suspending agent selected from the group consisting of water-soluble cellulose derivatives, gelatin, polyvinyl alcohol, starch, methyl vinyl ether-maleic anhydride copolymers, vinyl acetate-maleic anhydride copolymers, metal salts of carboxymethylcellulose and polyacrylic acids, and mixtures thereof; from 0.1% to 2% by weight of a wetting agent selected from the group consisting of polyoxyethylene alkyl ethers, polyoxyethylene alkyl esters, polyoxyethylene alkyl aryl ethers, sorbitan alkyl esters, polyoxyethylene-propylene glycol ethers, polyoxyethylenesorbitan alkyl esters, fatty acid monoglycerides, fatty acid soaps, sulfates, alkyl aryl sulfonates, dialkylsulfosuccinates, alkyl sulfonates, ethylene oxide adducts of alkylphenols, and mixtures thereof; and from 8% to 20% by weight of a polyalkylene glycol, said percentages being based on the weight of the suspension, and
   (b) homogenizing said suspension to form a stable initiator dispersion.

2. The process of claim 1 wherein in Step (b) the suspension is at a temperature in the range of 5° to 30° C. when it is homogenized.

3. The process of claim 1 wherein the suspension formed in Step (a) contains from 20% to 30% by weight of said initiator.

4. The process of claim 1 wherein the suspension formed in Step (a) contains from 1.5% to 2.5% by weight of a suspending agent.

5. The stable aqueous dispersion of a solid free radical-generating polymerization initiator that is the product of the process of claim 1.

* * * * *